United States Patent [19]
DiMarco

[11] Patent Number: 5,999,855
[45] Date of Patent: Dec. 7, 1999

[54] METHOD AND APPARATUS FOR ELECTRICAL ACTIVATION OF THE EXPIRATORY MUSCLES TO RESTORE COUGH

[76] Inventor: Anthony F. DiMarco, 37490 Hunters Ridge, Solon, Ohio 44139

[21] Appl. No.: 09/224,244

[22] Filed: Dec. 30, 1998

Related U.S. Application Data

[63] Continuation-in-part of application No. 09/031,756, Feb. 27, 1998, abandoned
[60] Provisional application No. 60/039,674, Feb. 28, 1997.

[51] Int. Cl.$^6$ .................................................... A61N 1/22
[52] U.S. Cl. ............................................................ 607/42
[58] Field of Search ................................ 607/2, 42, 72, 607/73

[56] References Cited

U.S. PATENT DOCUMENTS

| | | |
|---|---|---|
| 4,827,935 | 5/1989 | Geddes et al. . |
| 5,678,535 | 10/1997 | DiMarco . |

OTHER PUBLICATIONS

Dimarco, Romaniuk & Supinski, "Electrical Activation of the Expiratory Muscles to Restore Cough", Case Western Reserve University, pp. 1444–1471, 1995.

DiMarco, Romaniuk, Kowalski & Supinski, "Efficacy of Combined Inspiratory Intercostal and Expiratory Muscle Pacing to Maintain Artificial Ventilation", Case Western Reserve University, pp. 122–126, 1997.

American Lung Association, "American Review of Respiratory Disease", (An official journal of the American Thoracic Society Medical Section of the American Lung Association), Apr., 1993.

John Bach, M.D., et al., "Airway Secretion Clearance by Mechanical Exsufflation for Post–Poliomyelitis Ventilator–Assisted Individuals", Arch Phys Med Rehabil vol. 74, Feb. 1993.

Anthony F. DiMarco, et al., "Mechanical Action of the Interosseous Intercostal Muscles as a Function of Lung Volume", Am Rev Respir Dis, 1990.

Anthony F. DiMarco, et al., "Artificial Ventilation by Means of Electrical Activation of the Intercostal/Accessory Muscles Alone in Anesthetized Dogs", Am Rev Respir Dis, 1989.

Anthony F. DiMarco, et al., "Activation of the Inspiratory Intercostal Muscles by Electrical Stimulation of the Spinal Cord", Am Rev Respir Dis., 1987.

Erik Van Lunteren, et al., "Role of Triangularis Sterni during Coughing and Sneezing in Dogs", Dept. of Medicine, University Hospitals and Case Western Reserve University, The American Physiological Society, 1988.

(List continued on next page.)

*Primary Examiner*—Scott M. Getzow
*Attorney, Agent, or Firm*—Fay, Sharpe, Fagan, Minnich & McKee, LLP

[57] ABSTRACT

A method and apparatus are provided for electrical stimulation of the expiratory muscles in a human or other mammal to produce cough in patients with spinal cord injuries resulting in paralysis of their expiratory muscles. The method of electrically activating expiratory muscles of a human patient or other mammal includes positioning a first epidural electrode at a first location on the dorsal surface of a spinal cord of a patient and a second epidural electrode, if necessary, at a second location on the dorsal surface of the patient's spinal cord. The first epidural electrode is positioned on the spinal cord dorsal surface in the region of the $T_9$–$T_{10}$ spinal root level, while the second epidural electrode is positioned in the region of the lower thoracic spinal root, at the $T_{12}$–$L_1$ spinal cord level. Electrical stimulation pulses are selectively passed to the first and second epidural electrodes from an implanted radio-frequency receiver and stimulation pulse generator to activate expiratory muscles of the patient to produce cough. The invention provides a safe, effective, and portable means by which spinal cord injured patients are able to clear secretions more easily and thereby improve their lifestyle and reduce the morbidity and mortality due to respiratory complications.

12 Claims, 16 Drawing Sheets

OTHER PUBLICATIONS

Raymond Bellamy, M.D. et al., "Respiratory Complications in Traumatic Quadriplegia", Dept. of Neurological Surgery, Univ. of S. California School of Medicine, Nov., 1973.

Jewell L. Osterholm, M.D., "Electrothoracic Aretificial Respiration", Dept. of Surgery, Hahnemann Medical College, Philadelphia, PA.

Arthur A. Siebens, M.D. et al., "Cough Following Transection of Spinal Cord at C–6", Rehabilitation Center, University Hospitals University of Wisconsin.

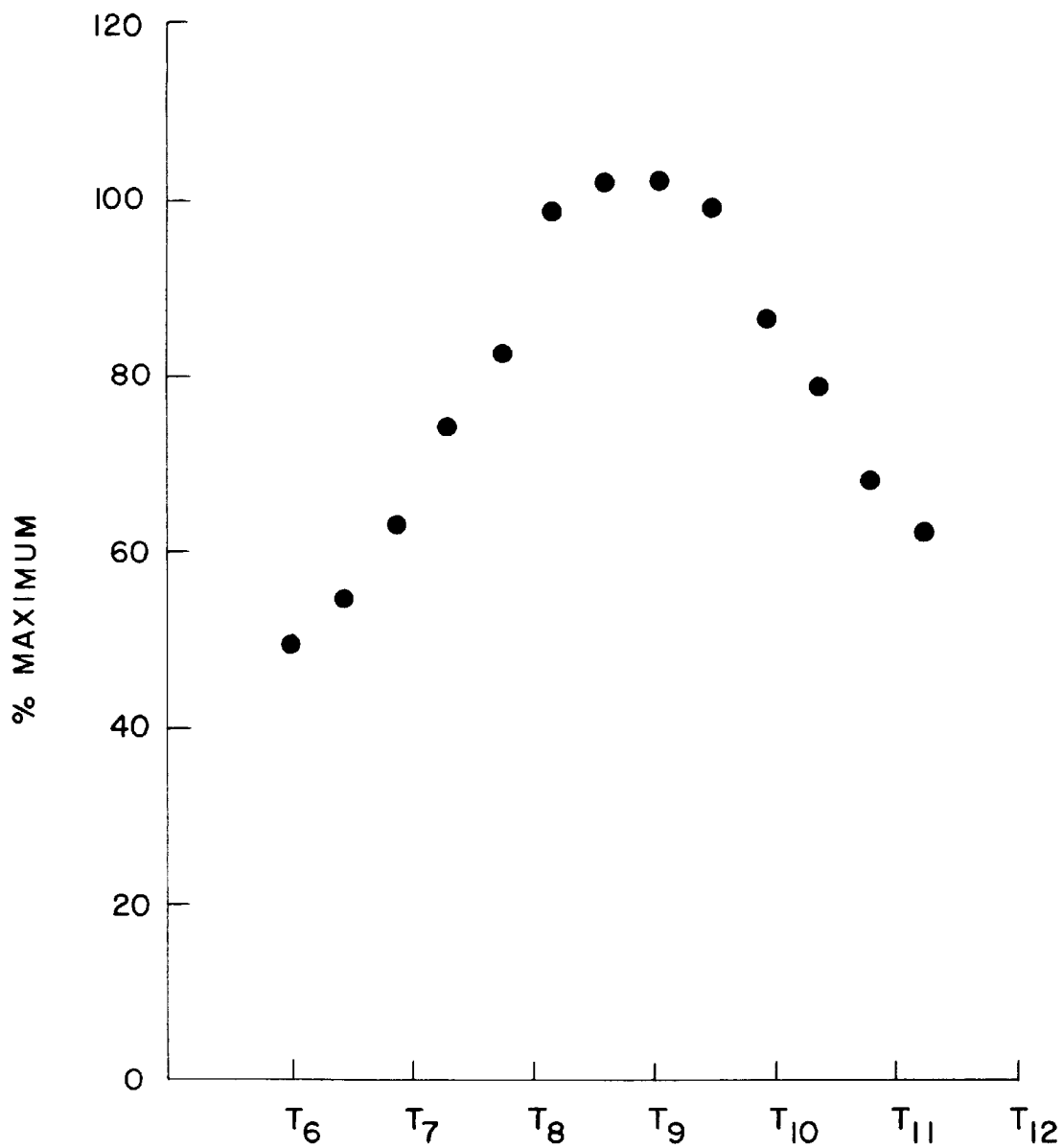
FIG. I

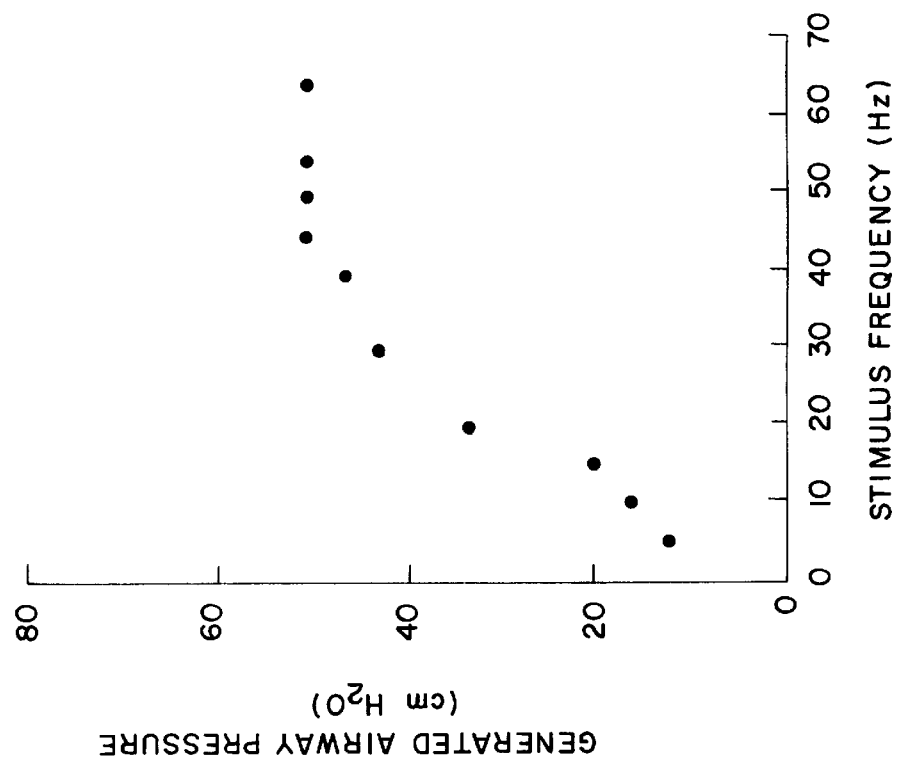
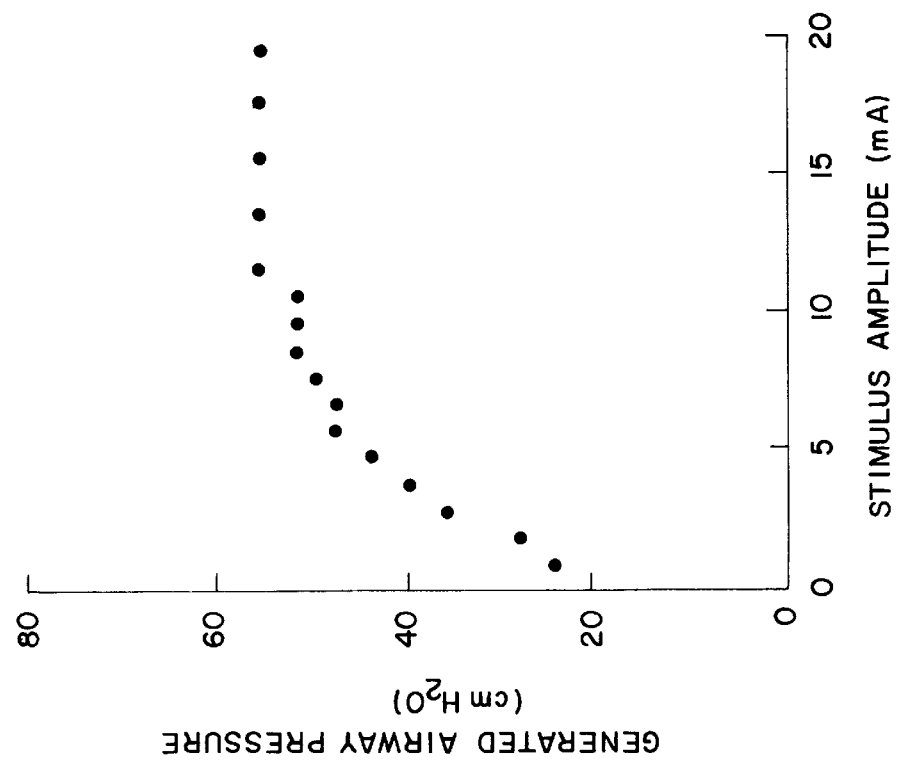
FIG. 2A
FIG. 2B

METHOD AND APPARATUS FOR ELECTRICAL ACTIVATION OF THE EXPIRATORY MUSCLES TO RESTORE COUGH

CROSS-REFERENCE TO RELATED APPLICATIONS

This application is a continuation-in-part (CIP) of U.S. application Ser. No. 09/031,756 filed Feb. 27, 1998, now abandoned, which claimed priority from U.S. provisional application Serial No. 60/039,674 filed Feb. 28, 1997.

BACKGROUND OF THE INVENTION

The present invention relates to electrical stimulation of the expiratory muscles to produce cough in human patients and other mammals with spinal cord injuries resulting in paralysis of their expiratory muscles. The invention will allow human patients with such spinal cord injuries to cough periodically or as needed to prevent the occurrence of respiratory infections which have heretofore been a frequent cause of illness and even death among this patient population.

Human patients with spinal cord injury often have paralysis of a major portion or virtually all of their expiratory muscles and, therefore, lack a normal cough mechanism. As a consequence, many of these patients suffer from a markedly reduced ability to clear airway secretions. This factor contributes to the development of recurrent respiratory tract infections, a major cause of morbidity and mortality in this patient population.

Although mechanical methods exist which can increase peak expiratory air flow to improve cough effort, the degree of improvement with these methods is small. For example, the abdominal push assist maneuver involves assisting a patient's expiratory effort by applying pressure with both hands to the upper abdomen in a posterior and cephalad direction. If abdominal pressure is applied following spontaneous inspiration and glottic closure, an adequate cough pattern may be achievable. This procedure has been found to result in modest increments in peak expiratory flow (in the range of approximately 14%) over that achieved without assist and no change in total volume during the cough.

Another prior mechanical technique is mechanical insufflation-exsufflation. This is carried out by the application of positive pressure to the patient's airway followed by rapid decompression, which results in the generation of high expiratory airflows. This technique may also be effective in removing foreign bodies from the patient's airway.

Although these prior techniques may be generally effective, a need has been found for more effective methods. A major disadvantage of these prior techniques is that they are dependent upon trained personnel and provider-patient coordination. Consequently, these methods are costly and labor intensive.

Heretofore, no effective method and apparatus have been found for selectively electrically activating expiratory muscles of a human patient or other mammal by stimulation of the spinal cord roots to produce a functionally effective cough. The only known prior method for electrical stimulation of the abdominal muscles is via surface electrodes over the anterior abdominal wall. This prior technique does not result in complete activation of the abdominal muscles which creates only submaximal cough efforts and requires high stimulus intensities.

Accordingly, it is deemed desirable to develop methods and apparatus which overcome the foregoing deficiencies and others while providing better and more advantageous overall results.

SUMMARY OF THE INVENTION

In accordance with the present invention, a method and apparatus are provided for electrical stimulation of the expiratory muscles in a human or other mammal to produce cough in patients with spinal cord injuries resulting in paralysis of their expiratory muscles.

In accordance with a first aspect of the present invention, a method of electrically activating expiratory muscles of a human patient or other mammal includes positioning a first epidural electrode at a first location on the dorsal surface of a spinal cord of a patient and a second epidural electrode at a second location on the dorsal surface of the patient's spinal cord. Electrical stimulation pulses are selectively passed to the first and second epidural electrodes to activate expiratory muscles of the patient to produce cough.

Preferably, the first epidural electrode is positioned on the spinal cord dorsal surface in the region of the $T_9$–$T_{10}$ spinal root level, while the second epidural electrode is positioned in the region of the lower thoracic spinal root. Most preferably, the second electrode is positioned on the dorsal surface of the spinal cord in the region of the $T_{12}$–$L_1$ spinal cord level.

One advantage of the present invention is found in the provision of an effective method and apparatus for selective electrical stimulation of the expiratory muscles to produce a cough in a human patient or other mammal having spinal cord injuries resulting in paralysis of the expiratory muscles.

Another advantage of the present invention is that it allows spinal cord injured patients to clear secretions more easily and thereby improve their lifestyle and reduce the morbidity and mortality due to respiratory complications.

Still another advantage of the present invention is that it provides for the optimal number of stimulation electrodes to produce the optimum contraction of the expiratory muscles.

Yet another advantage of the present invention is that it provides for optimal electrode placement for maximum expiratory pressure generation.

Still a further advantage of the present invention resides in its ability to provide a safe and effective means by which a normal and effective cough may be produced on demand without the need for the frequent presence of trained providers.

A yet further advantage of the present invention resides in the provision of a portable, battery-powered expiratory muscle stimulation apparatus that is able to travel with the patient in an easy and convenient manner.

Still further benefits and advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components. The drawings are only for purposes of illustrating preferred embodiments and are not to be construed as limiting the invention.

FIG. 1 is a graph illustrating the effect of electrode placement in a mammal on airway pressure generation;

FIG. 2A is a graph illustrating the effects of stimulus amplitude on airway pressure;

FIG. 2B is a graph illustrating the effects of stimulus frequency on airway pressure;

DETAILED DESCRIPTION OF THE PREFERRED EMBODIMENTS

Figure 3:
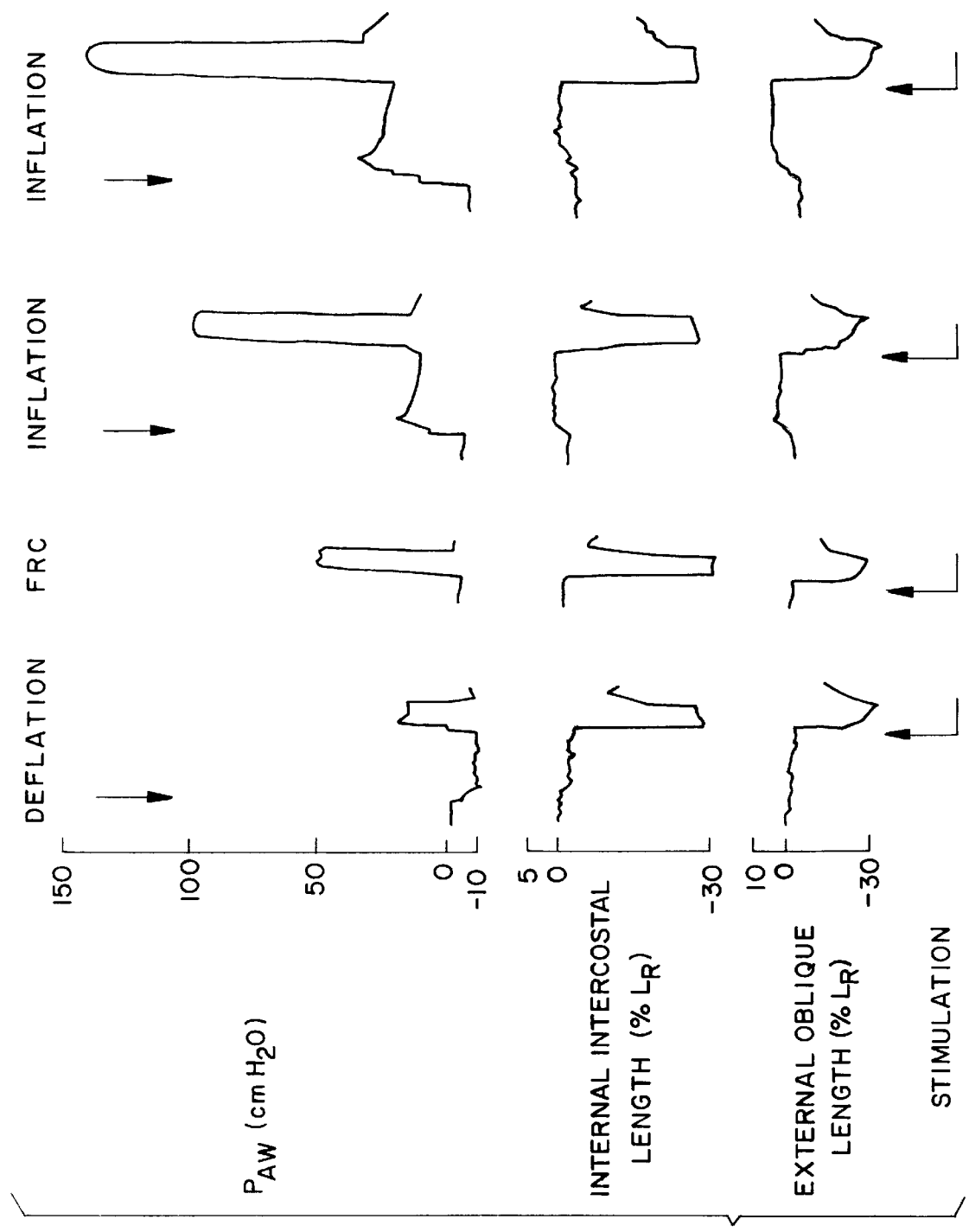
FIG. 3 is a graph illustrating the effect of spinal cord stimulation, as indicated by arrows, on internal intercostal (IIC) and external oblique (EO) muscle lengths and airway pressure generation with deflation, at functional residual capacity (FRC) and at two levels of inflation.

Referring now to the drawings, the showings are for purposes of illustrating preferred embodiments of the invention only and are not for purposes of limiting the same. Prior to application of spinal cord stimulation on human patients, and in order to develop the methods and apparatus of the present invention, it was necessary to evaluate the effects of motor root activation in animal studies. In this manner, it was possible to explore the utility of electrical stimuli applied to the lower thoracic region of the spinal cord to generate large changes in intrathoracic pressure and expiratory airflow, characteristic of cough. Further, it was necessary to assess optimum electrode placement, stimulus paradigm, and pattern of respiratory muscle recruitment since determination of these heretofore unknown variables was required prior to any human trials. Since the capacity of the expiratory muscles to generate force is dependent upon their precontractile lengths, studies were performed both at functional residual capacity (FRC) and over a wide range of static airway pressures. Muscle length measurements were also made to assess the degree and extent of expiratory muscle activation.

Methods

Studies were performed on 15 adult mongrel dogs (mean weight: 17.9 kg±0.4). Animals were anesthetized with pentobarbital sodium at an initial dose of 30 mg/kg given intravenously. Subsequent doses of approximately 2–4 mg/kg were provided as needed. All animals underwent a cervical tracheostomy and placement of a large bore cuffed endotracheal tube (inner diameter 10 mm). Blood pressure was monitored via a cannula placed in the femoral artery; a separate cannula in the femoral vein was used to administer additional anesthetic. The level of anesthesia was monitored by the corneal reflex which was suppressed. Body temperature was kept at 38±0.50° C. with a homeothermic blanket (Harvard Apparatus). Sodium bicarbonate was administered, as needed, to maintain blood pH at 7.35±0.05. A quadripolar platinum-iridium stimulating electrode (Medtronic Model 3586; Medtronic Inc., Minneapolis, Minn.) was inserted epidurally and on the ventral surface of the spinal cord via a $T_4$–$T_5$ laminectomy and then advanced caudally over the lower thoracic spinal cord. At this stage, a four-channel stimulator (Applied Neural Control Laboratory, Case Western Reserve University) was used for electrical stimulation. This stimulator provides a biphasic, pulse-width modulated impulse.

In seven animals, muscle length was measured with sonomicrometry. Pairs of piezoelectric crystals (Model 120, Triton Technology, San Diego, Calif.), spaced 5–12 mm apart and oriented along the long axes of muscle fibers, were sewn into the internal intercostal (IIC) (mid-axillary line) of the $9^{th}$ or $10^{th}$ intercostal space and external oblique (EO) muscles midway between the costal margin and pelvis. A small portion of the external intercostal and EO muscles were excised to provide access to the IIC muscles. Resting length was determined following hyperventilation induced apnea; changes in muscle length were expressed as a percentage of this value at FRC (percentage of resting length, % $L_R$).

Protocol

The effect of spinal cord stimulation (SCS) at different spinal cord levels was evaluated to determine optimal electrode placement. Also, the relationship between the stimulus parameters and airway pressure generation was determined. Changes in airway pressure during lower thoracic SCS were assessed following hyperventilation-induced apnea and airway occlusion. Electrical stimulation was applied at FRC and also over a wide range of lung volumes between approximately 0.3 liters below and 1.3 liters above FRC. Lung volume changes were produced by inflating and deflating the animal with a 2.0 liter volume syringe. A mean of 10±1 different volumes provided randomly were evaluated in each animal. These studies were performed in 15 animals.

After peak airway pressure was achieved consequent to spinal cord stimulation (SCS), the occlusion was released to assess expiratory airflow generation. This maneuver was also performed over a wide range of lung volumes. Studies were performed in 5 animals.

To assess the possibility of current spread more cephalad to activate the inspiratory intercostal muscles, spinal cord stimulation was performed before and after section of the parasternal muscles and also external intercostal muscles to the posterior axillary line from the $2^{nd}$ through $6^{th}$ interspaces. These studies were performed in 4 animals.

Data Analysis

Inflation and deflation produced a wide range of precontractile airway pressures between −14 and +35 cm $H_2O$. Precontractile static airway pressures were plotted against generated airway pressure and peak expiratory airflows produced by spinal cord stimulation in each animal. Changes in muscle length were expressed as a percentage of resting length (% $L_R$) and were analyzed in similar fashion.

Mean changes (±SE) in airway pressure, airflow, and muscle length resulting from spinal cord stimulation at specific precontractile airway pressures were then determined by interpolation of curves obtained from individual animals. Statistical analyses were performed utilizing a one-way analysis of variance and Student's t-test. A p value of <0.05 was considered significant.

Results

The effects of spinal cord stimulation in the region of the lower thoracic spinal cord is provided in FIG. 1. As shown, electrical stimuli applied at spinal cord level $T_9$–$T_{10}$ provided maximal changes in airway pressure generation. Stimulation above and below this region resulted in progressive reductions in airway pressure generation as the electrode was positioned more caudally or rostrally. Similar results were obtained in three other animals. In each subsequent animal, therefore, we sought to position the electrode in the $T_9$–$T_{10}$ region; the precise final electrode location was determined by that position which resulted in maximum positive airway pressure generation. By visual inspection and palpation, electrical stimulation in this area produced a marked symmetric contraction of the abdominal muscles and intercostal muscles of the lower rib cage bilaterally. There was no muscle contraction of the limbs nor visible contraction of the upper rib cage muscles.

The effects of alterations in stimulus amplitude (0.1 msec pulse width) and frequency on airway pressure generation at FRC is shown for one animal in FIG. 2A. Increasing stimulus amplitude at a constant stimulus frequency (50 Hz) resulted in progressive increases in airway pressure generation until a plateau was reached at approximately 10–12 mA. Repeated stimulation at higher amplitudes resulted in no further increases in airway pressure. Increasing stimulus frequency, as shown in FIG. 2B (at supramaximal stimulus amplitude), resulted in progressive increases in airway pressure generation until a plateau was reached at 40–45 Hz. Again, repeated stimulation at higher frequencies resulted in approximately the same changes in airway pressure. Similar results were obtained in the three other animals. In each animal studied, supramaximal stimulus parameters were determined initially, and all subsequent portions of the study were performed with that stimulus paradigm.

The effects of supramaximal spinal cord stimulation at the $T_9$–$T_{10}$ spinal cord level on airway pressure generation, and internal intercostal (IIC) and external oblique (EO) muscle length are shown for one animal in FIG. 3 (the lower arrows indicate the onset and duration of electrical stimulation; the upper arrows indicate the onset of inflation or deflation). At FRC, electrical stimulation resulted in a large positive deflection in airway pressure and marked shortening of both the IIC and EO muscles. With passive deflation, there was passive shortening of the IIC muscle and little change in EO muscle length. Subsequent electrical stimulation resulted in IIC and EO muscle shortening, similar to that which occurred at FRC, but a smaller increase in airway pressure. With passive inflation, both IIC and EO muscles lengthened; subsequent stimulation resulted in similar degrees of muscle shortening as that achieved at FRC and with deflation. As lung volume increased, however, airway pressure generation increased progressively.

Figure 4:
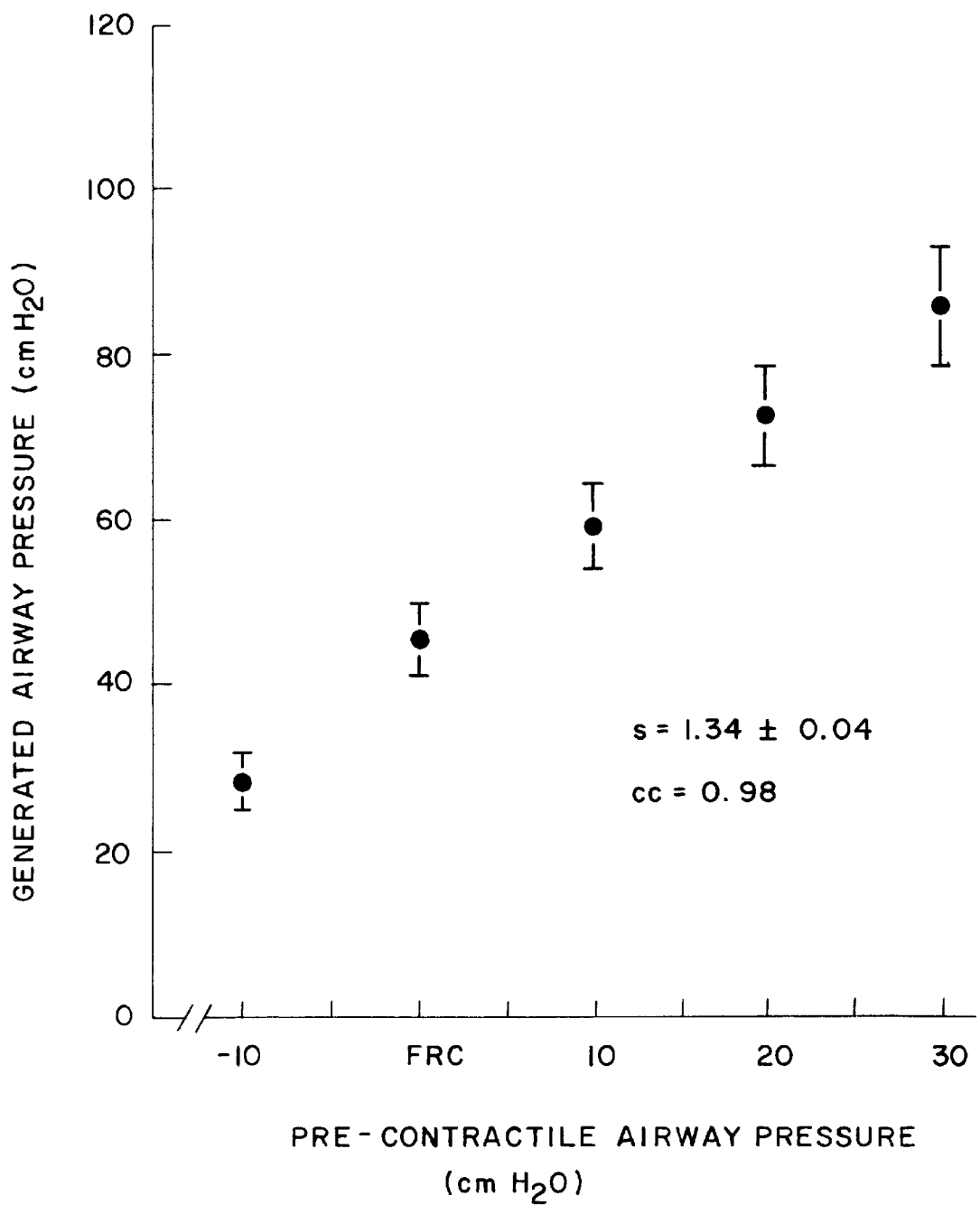
FIG. 4 graphically illustrates mean generated airway pressures as a function of pre-contractile airways.

The mean changes in airway pressure generation over a wide range of lung volumes is shown for one animal in FIG. 4. With increasing lung volume (expressed as the corresponding change in airway pressure), there were progressive increases in the magnitude of generated positive airway pressure according to a linear function (slope (s)= 1.34±0.04). In all animals, the range of correlation coefficients (cc) was between 0.89 and 0.99 (mean=0.97±0.01). The mean generated airway pressure at a passive inflation pressure of +30 cm $H_2O$ was 82 cm $H_2O$±7 SE, and in several animals exceeded 100 cm $H_2O$. In more recent studies, airway pressures have exceeded 175 cm $H_2O$.

During the performance of these studies, airway pressure generation was intermittently reassessed at FRC (5–7 times in each animal) to evaluate the reproducibility of the response and stability of the animal. The coefficient of variance was less than 10% in each animal.

Airway pressure generation was not significantly affected by parasternal and external intercostal muscle action. Mean airway pressure was 49 cm $H_2O$±13 SE before and 45 cm $H_2O$±10 SE after muscle section at FRC.

Figure 5:
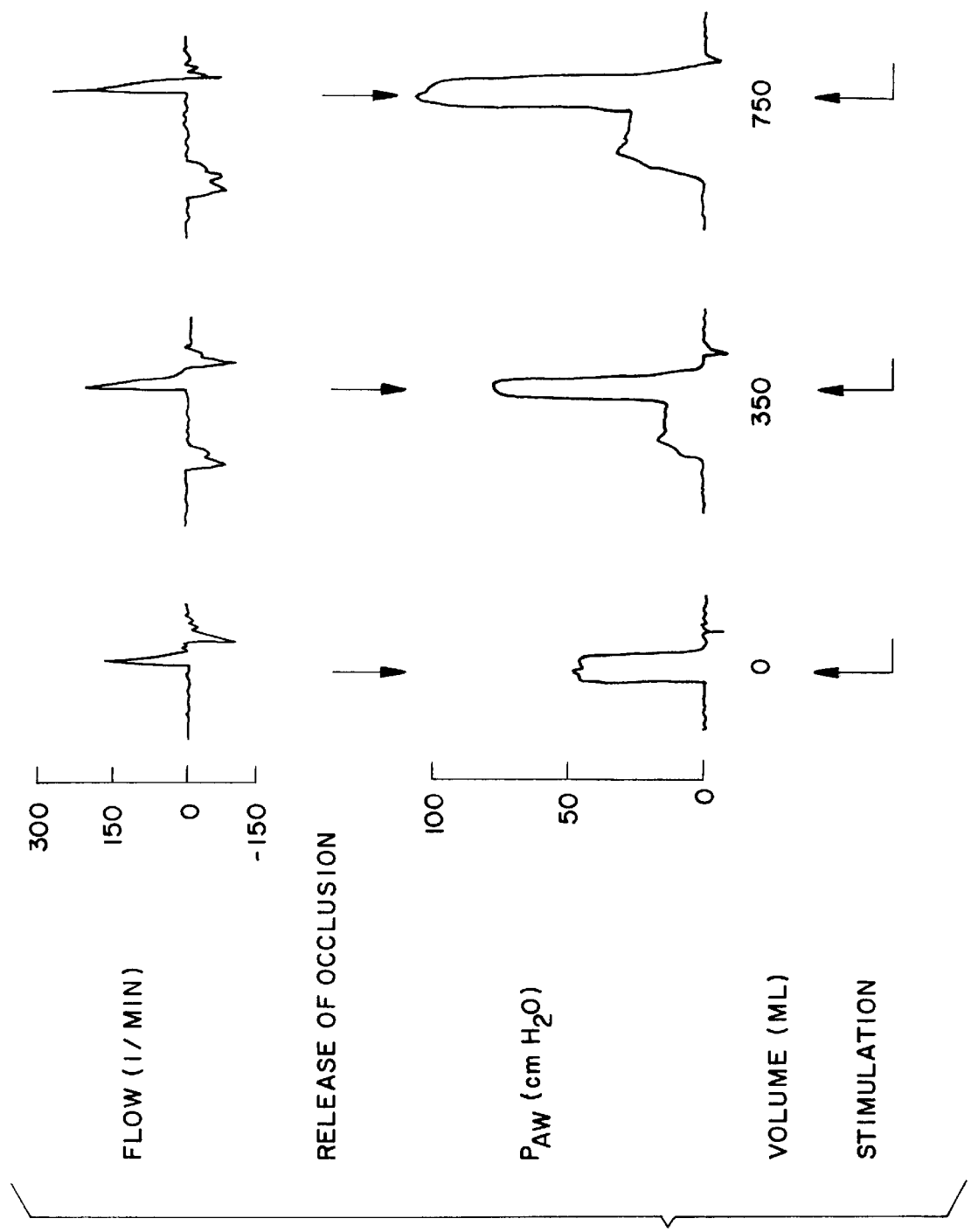
FIG. 5 is a graph illustrating the effects of spinal cord stimulation in a mammal on peak expiratory airflow at FRC and two levels of inflation.
Figure 6:
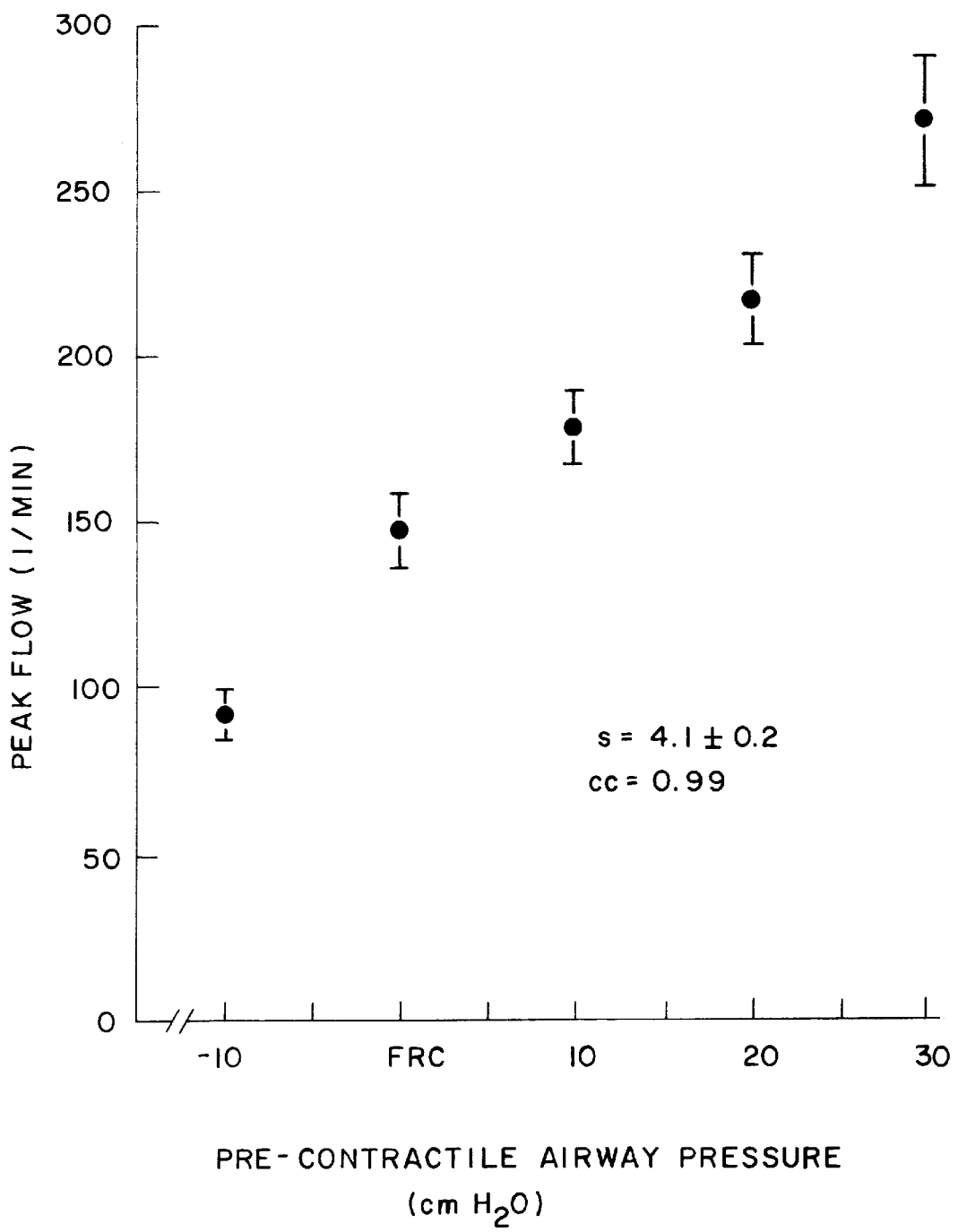
FIG. 6 graphically illustrates mean peak expiratory airflows as a function of pre-contractile airway pressures.

The effects of spinal cord stimulation on expiratory airflow generation are shown for one animal in FIG. 5 (the lower arrows indicate the onset and duration of electrical stimulation; the upper arrows indicate release of occlusion). Release of occlusion at FRC was associated with a peak flow rate of approximately 150 liters/minute. As lung volume was increased, spinal cord stimulation was associated with progressively greater peak airflow rates. The mean peak flows generated over a wide range of lung volumes are shown in FIG. 6. With increasing lung volume, there were progressive increases in peak airflow generation according to a linear function (slope=4.1±0.2).

Figure 7:
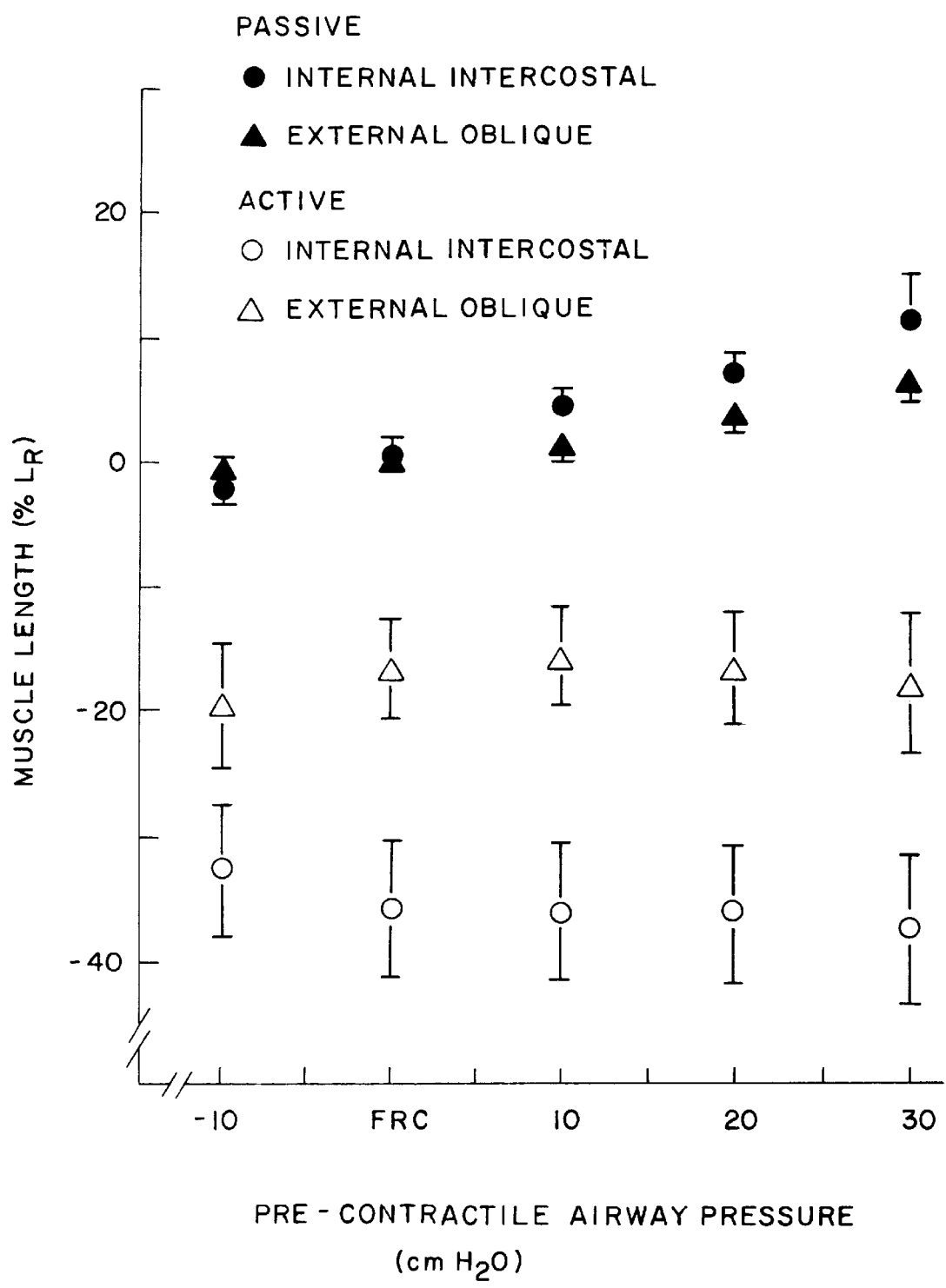
FIG. 7 graphically illustrates mean changes in internal intercostal and external oblique muscle length with passive inflation and deflation (solid symbols) and during spinal cord stimulation (open symbols) over a wide range of lung volumes.

The mean changes in muscle length as a result of passive inflation and deflation (solid symbols) are shown in the upper portion of FIG. 7. Both IIC and EO muscles shortened with passive deflation and lengthened progressively with increasing inflation in each animal. The magnitude of passive IIC lengthening at airway pressures of 20 and 30 cm $H_2O$ were significantly greater than that of EO (P<0.05). During supramaximal ventral root stimulation (open symbols), the IIC shortened to approximately 35–40% of resting length, while the EO shortened to approximately 20% of resting length (P<0.05). The degree of muscle shortening, however, did not vary significantly with lung volume for either muscle.

Discussion

It was apparent from the foregoing that a major portion of the expiratory muscle mass in mammals, including the abdominal muscles and the internal intercostal (IIC) muscles of the lower rib cage, can be activated reproducibly and in concert via lower thoracic spinal cord stimulation. The capacity of the expiratory muscles to produce changes in airway pressure and expiratory airflow varies markedly with lung volume; airway pressure and airflow generation are maximal at the highest inflation pressure and fall linearly with decreasing lung volume. Based upon the foregoing, it was determined that this electrical spinal cord stimulation technique can be a useful method of restoring cough in certain human patients with spinal cord injury and may also be a useful tool in assessing the mechanical properties of the expiratory muscles.

Mechanism of Muscle Activation

Initially, it was unclear exactly by which mechanisms the expiratory muscles were activated by the application of electrical stimuli in the region of the lower thoracic spinal cord. The mechanisms were thought to include: a) activation of spinal cord pathways and motoneurons, either directly or via spinal cord reflex pathways; b) direct activation of the ventral roots; or c) some combination of each of these pathways. Stimulation of descending motor tracts seemed unlikely, however, since activation of those tracts would be expected to produce a more generalized pattern of discharge and result in contraction of the lower limbs. It was determined that further studies were necessary to determine the specific path of current flow which results in expiratory muscle activation.

Patterns of Muscle Activation

Based upon previous experience with similar stimulus paradigms applied in the region of the upper thoracic spinal cord, electrical current spreads across several spinal segments both cephalad and caudal to the site of electrode placement. Since the electrode was positioned at the $T_9$–$T_{10}$ spinal cord level in the present studies, we would expect current spread to activate roots as high as the $T_6$ spinal level and caudally to activate the lower thoracic spinal roots. Based upon this degree of current spread, this should result in activation of the intercostal muscles of the lower rib cage ($T_7$–$T_{12}$) and the abdominal muscles (external and internal oblique, transversus abdominis and rectus abdominis) which are enervated by branches of the lower thoracic nerves.

Ideally, any technique to restore cough in humans and other mammals should result in activation of the expiratory muscles alone. Electrical current applied in the region of the lower thoracic spinal cord, however, provides a non-specific motor stimulus. The thoracic spinal nerves are mixed motor nerves enervating both inspiratory and expiratory muscles. While the internal intercostals of the lower rib cage (expiratory in action) were clearly activated, the external intercostal and levator costae muscles (inspiratory in action) of the lower rib cage were most likely stimulated, as well. It is unlikely, however, that external intercostal and levator costae activation resulted in any significant opposing action. In the lower rib cage, the external intercostals are very thin muscles and, in addition, do not encompass the entire interspace. The levator costae muscles are small flat spindle-shaped muscles located posteriorly. The internal intercostals (expiratory in function), on the other hand, are thick muscles over this region of the rib cage (approximately 3 mm) and encompass the entire space.

Current spread to the upper thoracic ventral roots ($T_1$–$T_6$) would have resulted in activation of inspiratory muscles of the upper rib cage, and generation of negative swings in airway pressure. It is unlikely, however, that current was transmitted this far cephalad since section of the parasternal and external intercostal muscles had no significant effect on airway pressure generation. At lung volumes above FRC, activation of the inspiratory intercostals is of much less concern since the capacity of these muscles to produce a fall in airway pressure declines rapidly as lung volume increases (12).

Significant portions of the triangularis sterni (TS) muscle were clearly not activated since parasternal section had no effect on airway pressure generation and the TS muscle is also enervated by the same internal intercostal nerves. Previous studies suggest, however, that the abdominal muscles are the major force generators and, of these, the transversus abdominis is the most important. While length measurements of this latter muscle were not made (to minimize the degree of surgery), its activation is likely due to the pattern of current spread. During spontaneous cough induced by mechanical stimulation of the trachea, however, it has been demonstrated that the electrical activation of both the triangularis sterni and transversus abdominis increase substantially. It has also been found that the electrical activation of these muscles peaked simultaneously during cough.

Although the foregoing technique clearly did not result in activation of all the expiratory muscles, the portion of expiratory muscle mass being stimulated was maximally activated. This is evidenced by the fact that with increasing stimulus frequency and amplitude, a plateau in airway pressure generation was achieved. Furthermore, the stimulus frequency and amplitude/response curves are qualitatively similar to that observed with either phrenic nerve stimulation or inspiratory intercostal muscle stimulation.

This above-described technique therefore provides a method by which a major portion of the expiratory muscles of a human or other mammal can be activated in reproducible fashion by positioning a single electrode on the ventral surface of the spinal cord.

Muscle Length Changes

Both the internal intercostal (IIC) muscles and external oblique (EO) muscles lengthened progressively with inflation and shortened with deflation, consistent with the action of expiratory agonists. The degree of passive muscle length changes was consistent with previous observations. Previous studies have shown that the internal layer of abdominal muscles (transversus abdominis and internal oblique) demonstrated significantly greater passive lengthening with inflation than the external layer (external oblique and rectus abdominis muscles). Because the transversus is thought to be the major force generator, the greater passive changes in resting length may be responsible, to some extent, for the large difference in airway pressure change between high and low lung volumes.

The EO muscles shortened by 15–20% of resting length while the IIC muscle shortened 35–40% of resting length in response to spinal cord stimulation. The degree of EO shortening with stimulation is far greater than the degree of shortening observed (<5%) with expiratory threshold loading and hypercapnia (90 mmHg), but less than the approximately 40% shortening observed when this muscle was stimulated directly in isolation. The maximum degree of EO shortening during spinal cord stimulation may be less, however, when all of the expiratory muscles are contracting in concert. For example, the increase in intra-abdominal pressure caused by IIC and transversus abdominous muscle contractions may oppose shortening of the abdominal muscles.

The foregoing indicates the feasibility of spinal cord stimulation to produce cough. However, single electrode stimulation as described above has been found to be suboptimal. In particular, while large positive airway pressures can be generated by spinal cord stimulation to restore cough in spinal cord injured human patients and other mammals, optimal electrode placement was not apparent from the foregoing and required an assessment of the pattern of electrical current spread during spinal cord stimulation.

Figure 8:
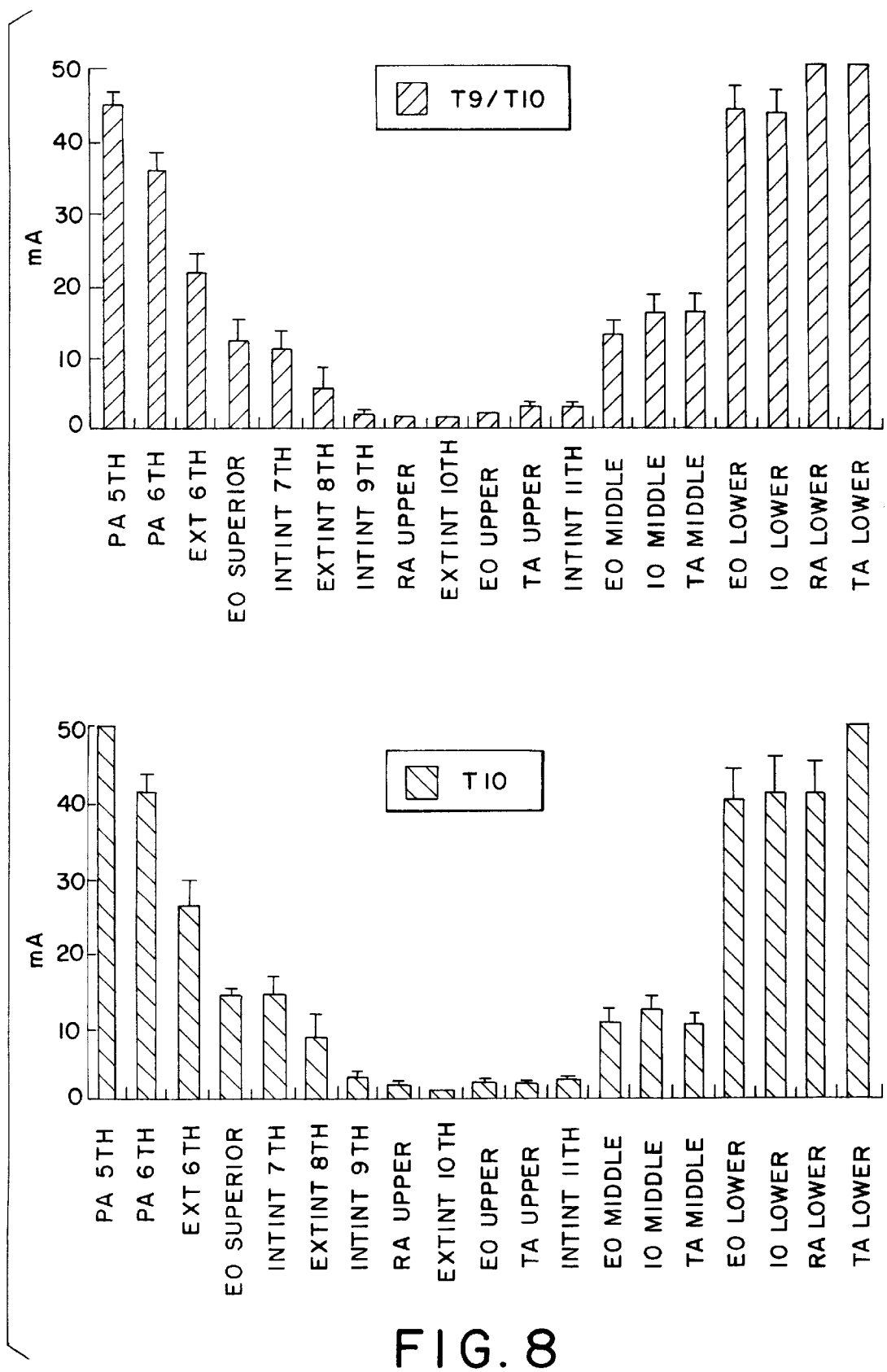
FIG. 8 illustrates that threshold values for the IIC ($7^{th}$–$11^{th}$ spaces) for the upper portions of EO, RA and TA were near their minimum at the $T_9$–$T_{10}$ spinal cord level.
Figure 9:
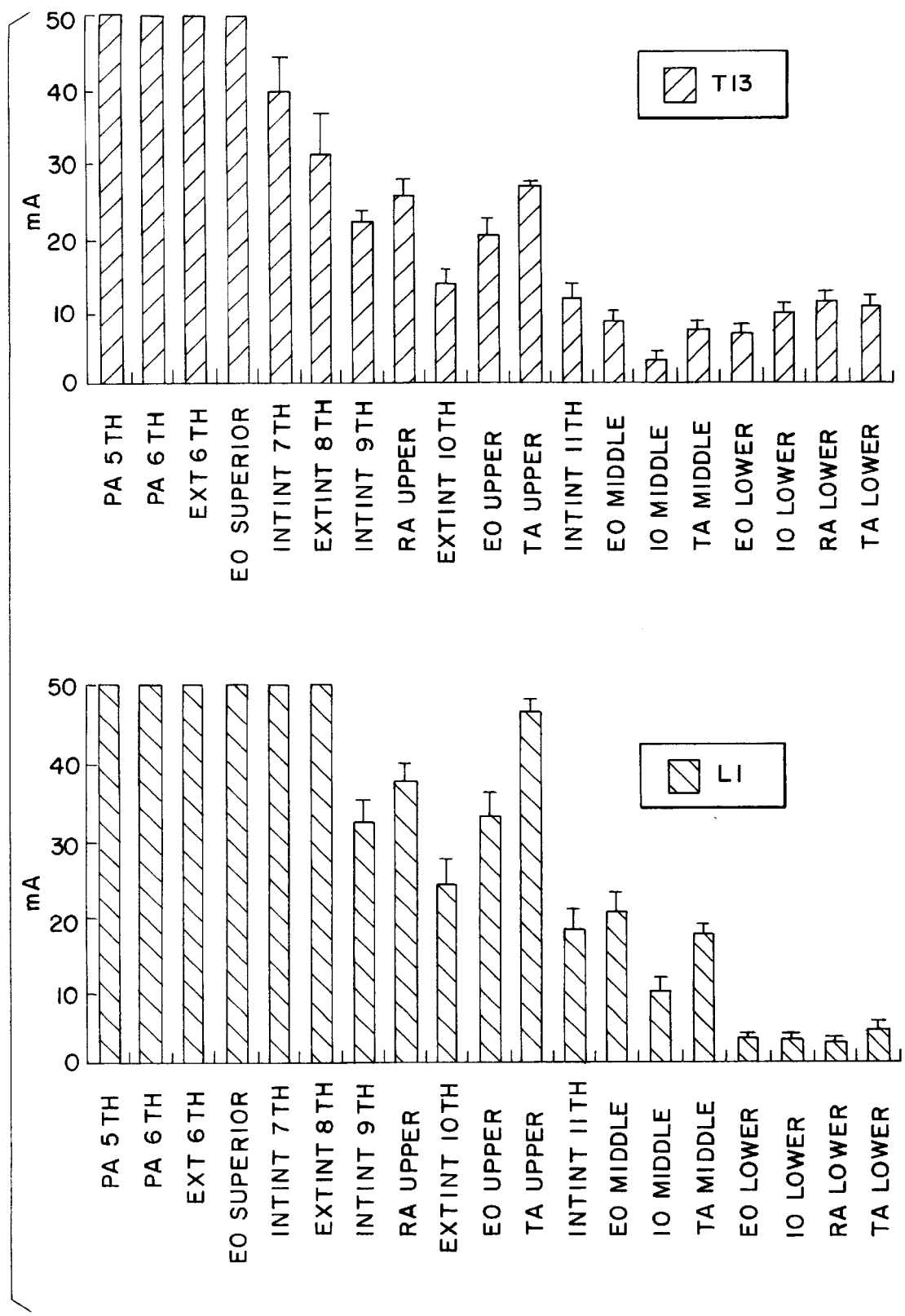
FIG. 9 illustrates that threshold values of the compound action potential for the IO and lower portions of the EO and TA were near their minimum at the $T_{13}$–$L_1$ spinal cord region (corresponding to $T_{12}$–$L_1$ for humans)

Studies were performed in six anesthetized dogs to assess the pattern of expiratory muscle recruitment during spinal cord stimulation applied at different spinal cord levels. A multicontact stimulating electrode was positioned over the surface of the lower thoracic and upper lumbar spinal cord. Recording electrodes were placed in the upper and lower portions of the transversus abdominis (TA), external oblique (EO), internal obliques (IO), rectus abdominis (RA) and the internal intercostal muscles (IIC). Spinal cord stimulation was applied at each lead, in separate trials, with single shocks, 0.1–0.2 msec duration. The intensity of stimulation was adjusted to determine the threshold for development of the compound action potential (CAP) at each electrode lead. The threshold for activation of each muscle formed parabolas with minimum values at specific spinal root levels. With reference to FIG. 8, it is shown that at the $T_9$–$T_{10}$ spinal cord level (which results in maximum positive pressure generation), threshold values for the IIC ($7^{th}$–$11^{th}$ spaces) upper portions of EO, RA and TA were near their minimums. The slopes of the parabolas were relatively steep indicating that the threshold for muscle activation increases rapidly at more cephalad and caudal sites. Threshold values of the CAP for the IO and lower portions of the EO and TA were near their minimum at the $T_{13}$–$L_1$ spinal cord region (FIG. 9). At the $T_9$–$T_{10}$ spinal cord level, threshold values for activating these latter muscles was high (>25 mA).

The results indicated that very high current levels at the $T_9$–$T_{10}$ level (>40 mA) or the use of more than one electrode would be necessary to achieve uniform expiratory muscle activation as is required for effective cough via electrical spinal cord stimulation.

Figure 10:
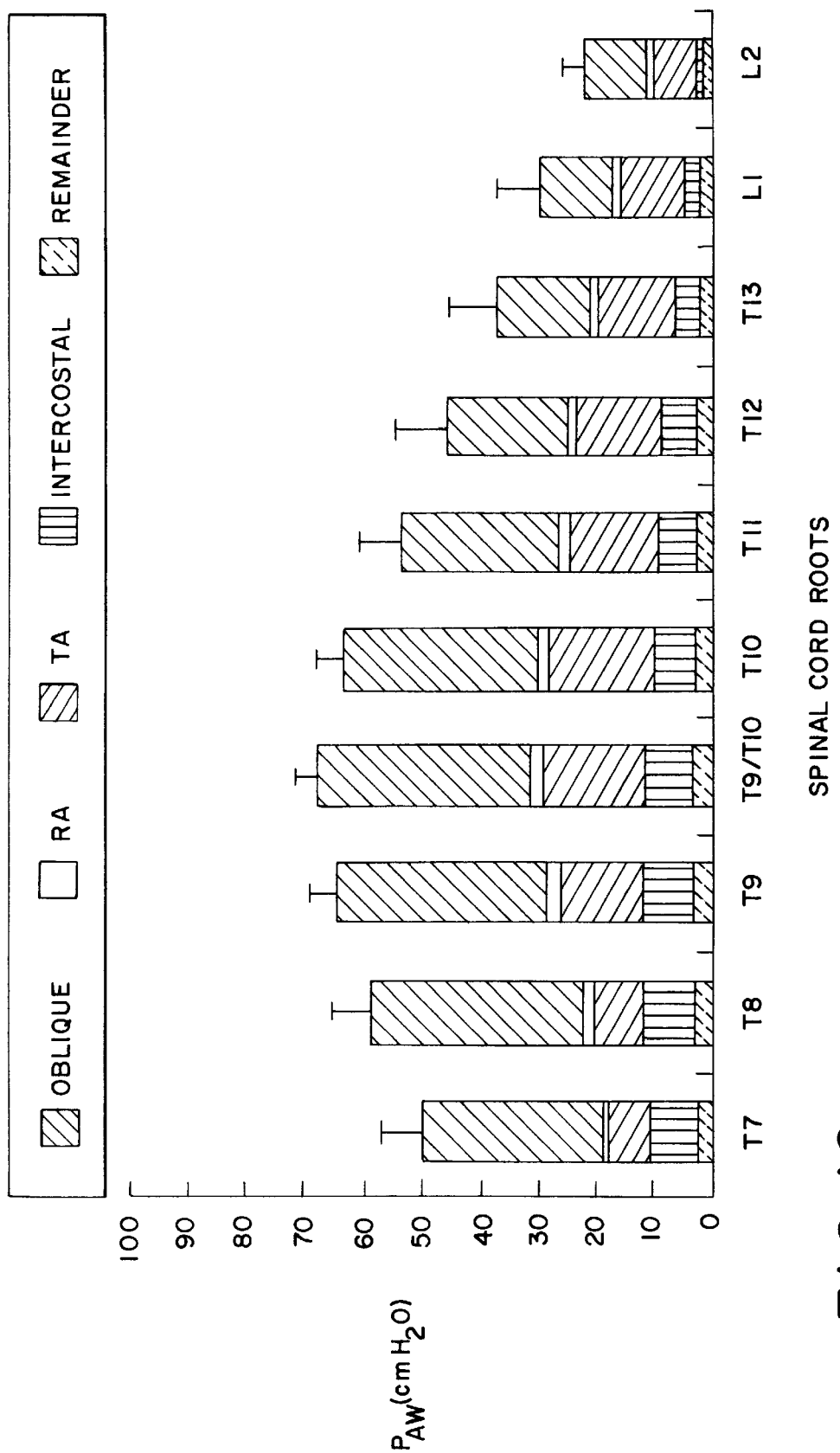
FIG. 10 shows the mean contribution of various expiratory muscles to pressure generation from stimulation at different spinal root levels.

However, it was also necessary to determine the mechanical contribution of the individual expiratory muscles to pressure generation during spinal cord stimulation. To do so, five anesthetized dogs were utilized. Spinal cord stimulation (15 mA) was applied at several different levels using a midline multicontact electrode before and after sectioning different groups of respiratory muscles. Airway pressure (P) was monitored following tracheal occlusion. Mean contribution of various expiratory muscles to pressure generation by stimulation at different spinal root levels is shown in FIG. 10. Electrical stimulation at the $T_9$–$T_{10}$ spinal cord level resulted in maximum P of 53 cm $H_2O$±5 SE. Ablation of the obliques (external and internal, OB), rectus abdominis (RA), transversus abdominis (TA) and internal intercostals of the lower rib cage (IIC) resulted in 51±3, 5±2, 26±3, and 13%±1 SE reductions in pressure generation, respectively. Stimulation at other sites resulted in significantly smaller P. During stimulation at $T_7$, P was 27 cm $H_2O$±6 SE (p<0.05) and ablation of OB, RA, TA and IIC resulted in 41±13, 4±2, 12±9, and 43%±12 SE reductions in pressure generation. During spinal cord stimulation at $L_1$, P was 22±5 cm $H_2O$ (p<0.05 compared to T9) and ablation of OB, RA, TA, and IIC resulted in 50± 5, 3±1, 38±5, and 6%±3 SE reductions in P.

Figure 11:
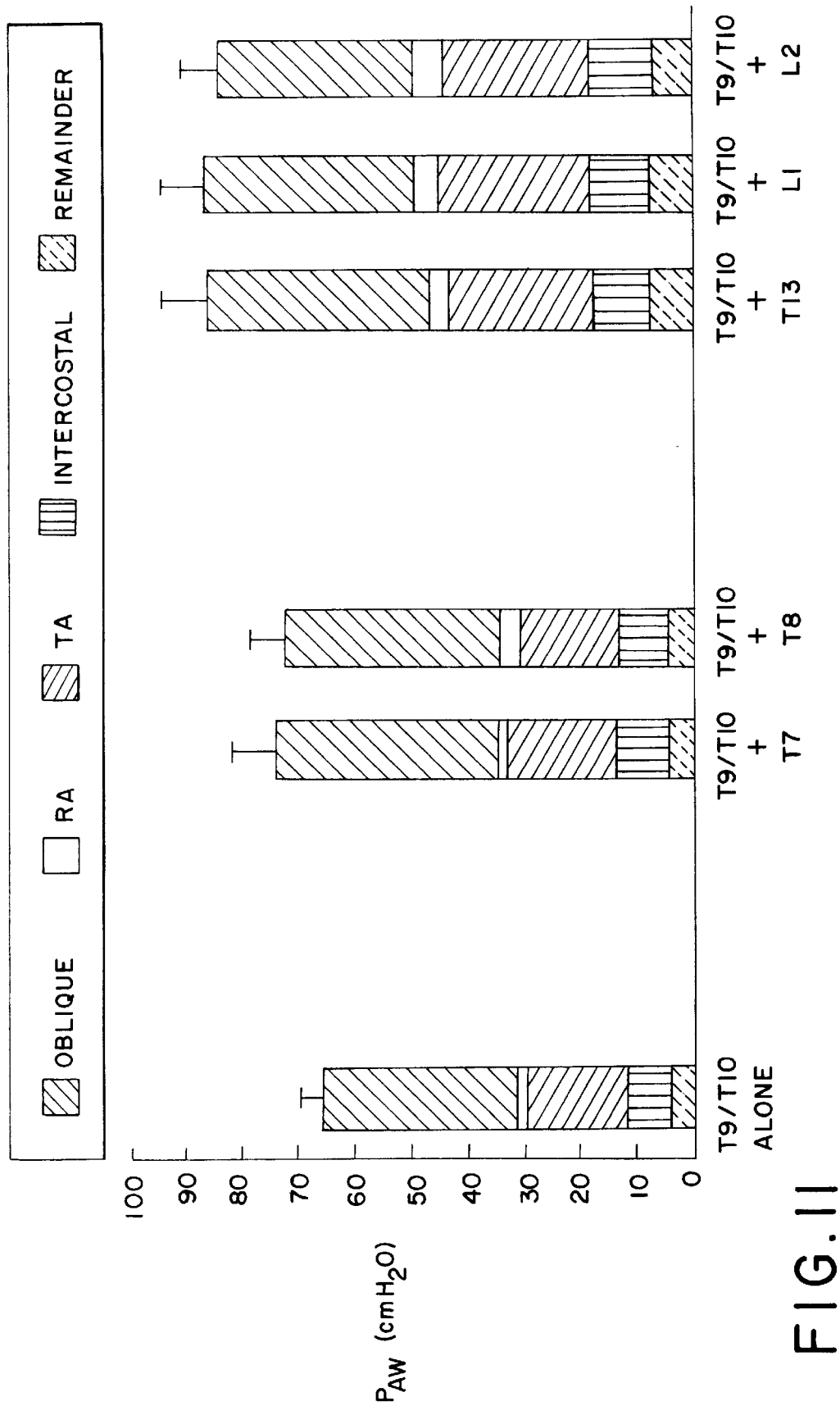
FIG. 11 shows mean airway pressure generation and contribution of the various expiratory muscles to pressure generation during stimulation applied to the $T_9$–$T_{10}$ spinal root level plus the simultaneous application of current to another spinal root level.

FIG. 11 illustrates mean airway pressure generation and the contribution of the various expiratory muscles to pressure generation during stimulation applied to the $T_9$–$T_{10}$ spinal root level plus the simultaneous application of current to another spinal root level. When simultaneous stimulation was applied with a second electrode in the same vicinity as the first ($T_9$–$T_{10}$), there were only small increments in pressure production (NS). However, the simultaneous application of current with a second electrode in the region of the lower thoracic spinal root ($T_{13}$–$L_1$) resulted in significant increases in pressure production (p<0.05). This increase in pressure production with the two electrode system resulted largely from increased contributions from both the obliques and transversus muscles. Those skilled in the art will recognize that human patients do not have a $T_{13}$–$L_1$ spinal cord level, but that the human spinal cord level of $T_{12}$–$L_1$ corresponds thereto. In human patients and other mammals that are particularly large and have a longer spinal cord, a third epidural electrode is advantageously used to counteract the effects of stimulation current dissipation over longer distances. Most preferably, the third electrode is positioned on the dorsal surface of the spinal cord in the region between the aforementioned first and second electrodes. Furthermore, it has been found most desirable to substantially simultaneously pass electrical stimulation pulses to all the electrodes at a frequency in the range of approximately 20 Hz–50 Hz wherein each pulse has an amplitude in the range of approximately 10 mA–40 mA.

The foregoing indicates that the external and internal obliques (OB) and the transversus abdominis (TA) make the largest contribution to airway pressure (P) during spinal cord stimulation at $T_9$–$T_{10}$ and the reduction of P at other sites was secondary to reductions in expiratory agonist activation rather than activation of antagonists. This data, coupled with recent electromyographic (emg) studies indicates that upper abdominal and internal intercostals of the lower rib cage (IIC) stimulation make a larger contribution to pressure generation compared to lower abdominal muscle stimulation.

In order to apply the foregoing to human patients and other mammals, it was deemed necessary and desirable to determine the particular mechanism of significant expiratory pressure generation (cough effort) by these electrical stimulation methods. Therefore, it was necessary to study the mechanism of expiratory muscle activation via lower thoracic spinal cord stimulation ($T_9$–$T_{10}$ region).

Figure 12:
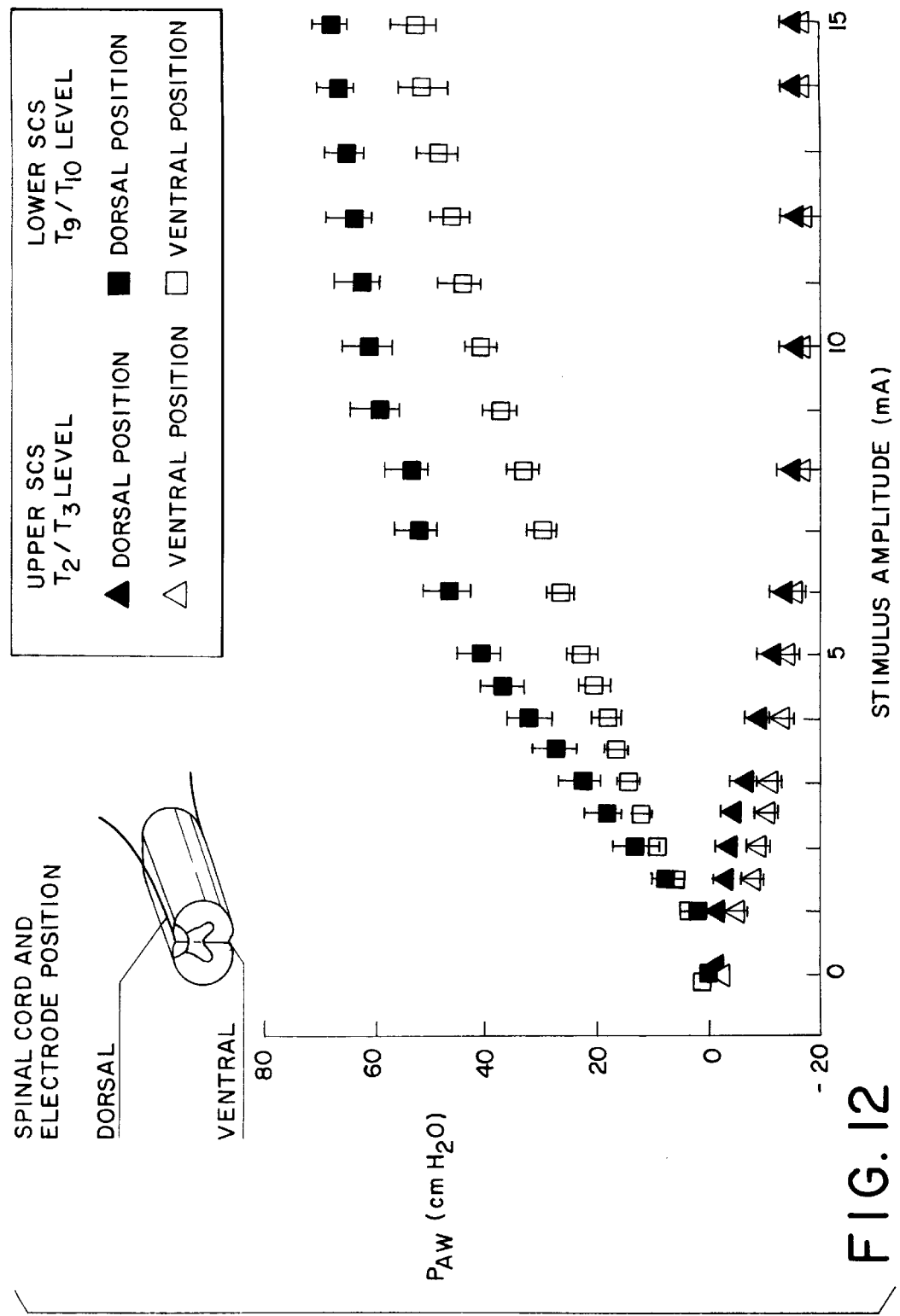
FIG. 12 graphically illustrates the contrast between upper and lower thoracic spinal cord stimulation with respect to the effect of dorsal vs. ventral placement of the stimulation electrode.

Using seven anesthetized dogs, airway pressure (P) changes during stimulation against an occluded airway were used and an index of the degree of expiratory muscle activation. With reference now also to FIG. 12, in contrast to upper thoracic spinal cord stimulation, dorsal placement of the stimulation electrode resulted in greater changes in P compared to ventral placement over a wide range of stimulus amplitudes. Dorsal spinal cord stimulation following section of all spinal roots between $T_8$ and $L_2$ resulted in a marked fall in P to 15 cm $H_2O$±1 SE (p<0.01).

In other studies with the spinal roots intact, the effects of transection of the spinal cord at the $T_{11}$ level were assessed. Spinal cord section resulted in large decrements in P from 54 cm H2O±2 SE to 21 cm H2O±2 SE. From this, it was determined that stimulation of the descending pathways localized near the dorsal surface of the spinal cord is an important mechanism of expiratory muscle activation via lower thoracic spinal cord stimulation.

Figure 13:
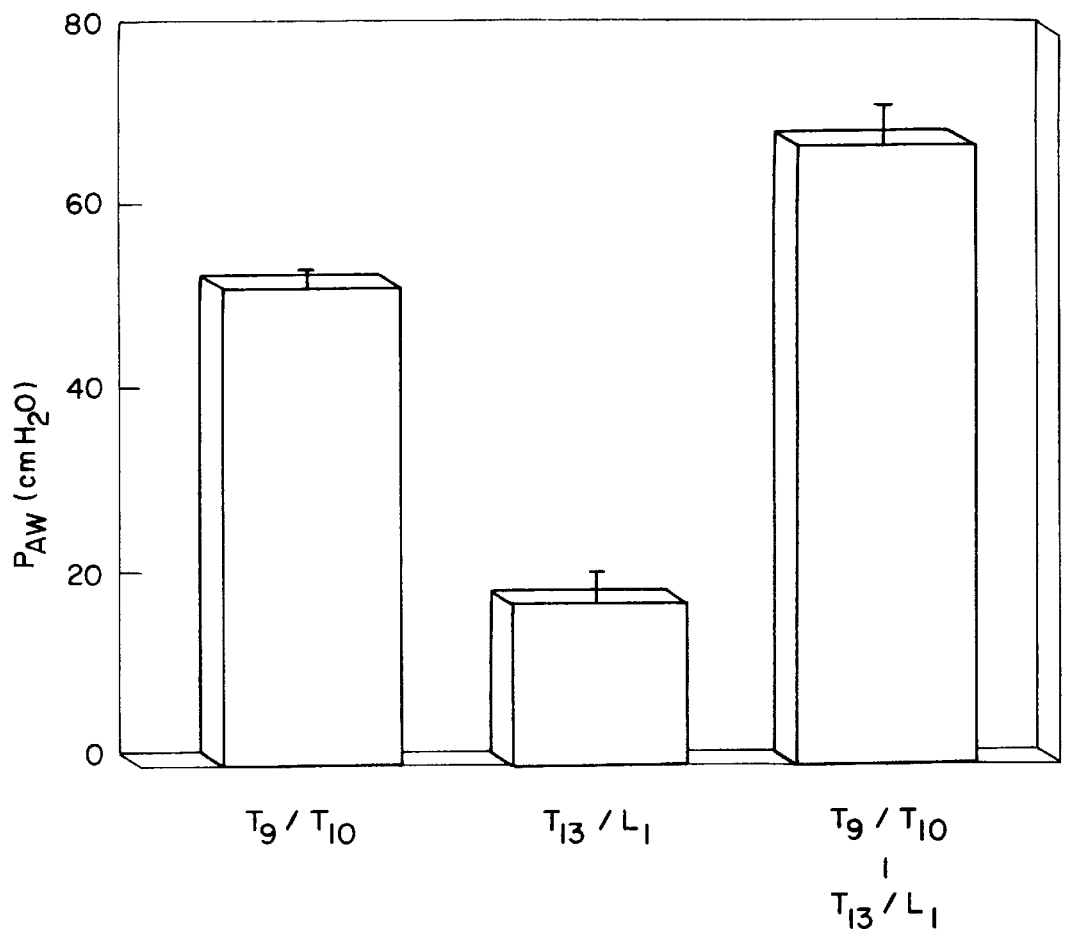
FIG. 13 illustrates the synergistic effect on pressure generation resulting from optimal multiple electrode placement and simultaneous stimulation in accordance with the method of the present invention.

In light of the foregoing, it was deemed necessary and desirable to study further the mechanism of airway pressure generation during lower thoracic spinal cord stimulation, in particular, the effect of synchronous activation of the musculature of both the upper and lower portions of the abdominal wall. In seven anesthetized dogs, spinal cord stimulation was applied with one electrode at the $T_9$–$T_{10}$ (upper) and another at the $T_{13}$–$L_1$ (lower) region of the spinal cord. During separate stimulation of the upper and lower electrodes, P was 55 cm $H_2O\pm2$ SE and 16 cm $H_2O\pm3$ SE, respectively. As is shown in FIG. 13, combined stimulation generated pressures that were larger than those produced by $T_9$–$T_{10}$ stimulation alone, indicating that $T_9$–$T_{10}$ stimulation alone is suboptimal.

To eliminate the potential influence of spinal cord pathways and assess the effects of local motor root activation alone, spinal cord stimulation was applied following section of the spinal roots ($T_8$–$L_2$). During separate stimulation at $T_9$–$T_{10}$ and $T_{13}$–$L_1$, alone, P was 12±2 and 15±3 cm $H_2O$, respectively. However, combined stimulation via the upper and lower electrodes together resulted in P=50±2 cm $H_2O$, a marked synergistic effect (P<0.05; compared to the arithmetic sum). In addition, following the application of an inelastic band around the lower portion of the abdominal wall, P during upper motor root stimulation alone increased to 22±3 cm $H_2O$ (P<0.05).

From this, it can be seen that: a) contraction of one portion of the abdominal wall alone results in dissipation of P via expansion of the non-contracted part of the abdominal wall, and b) synchronous activation of both the upper and lower portions of the abdominal wall is necessary to produce substantial changes in P. Furthermore, since P during $T_9$–$T_{10}$ stimulation was much greater in the intact compared to the denervated state and also similar to combined stimulation by the upper and lower electrodes, it is shown that stimulation at the $T_9$–$T_{10}$ region results in activation of the lower portion of the abdominal wall via spinal cord pathways.

To further explore and demonstrate the advantages of the foregoing methods over non-invasive stimulation methods in restoring cough in spinal cord injured patients, a comparison of the foregoing spinal cord stimulation methods with surface stimulation of the abdominal wall (SA) and also electrical surface stimulation of the spinal nerves (SN) was carried out.

Figure 14:
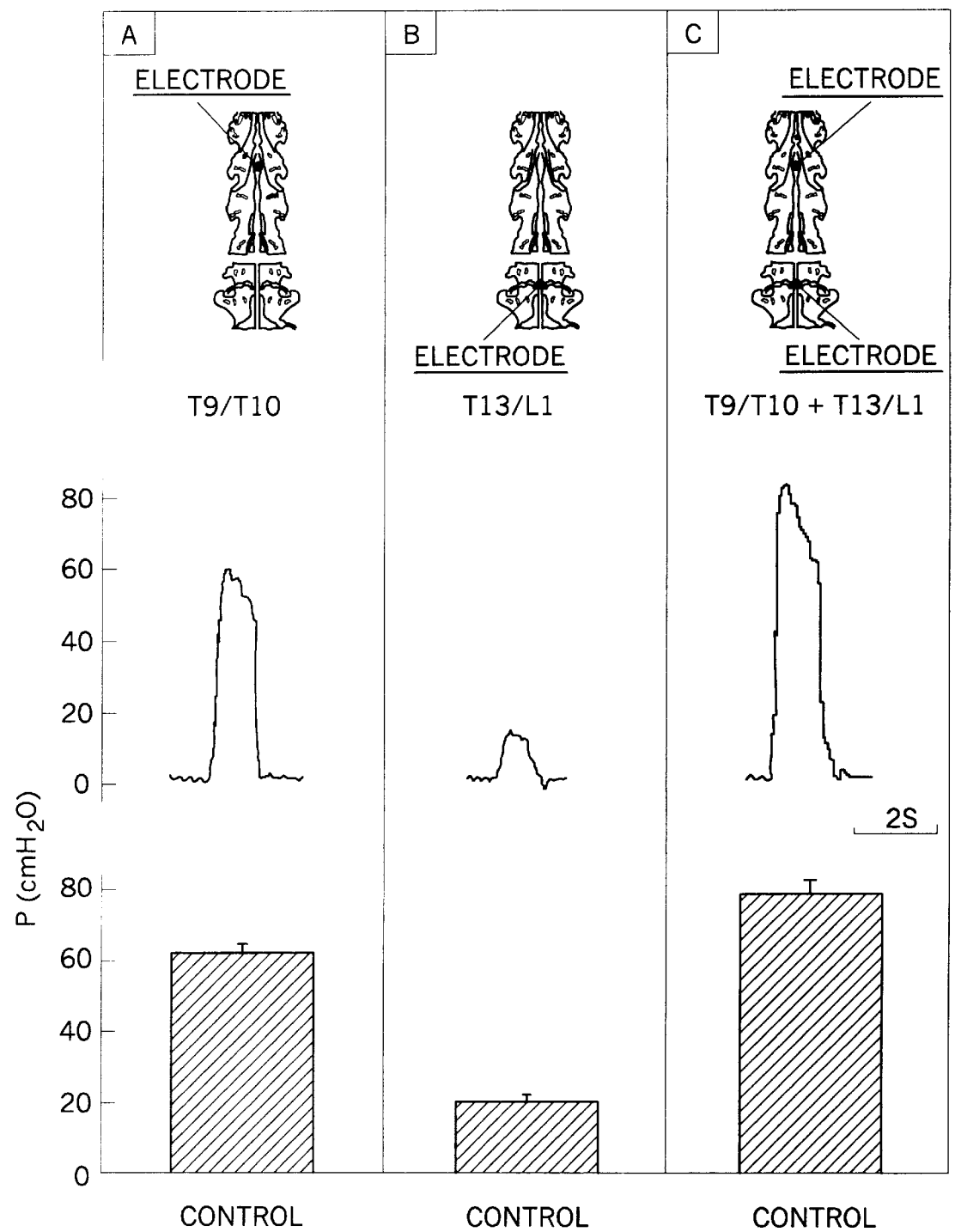
FIG. 14 illustrates the effects of epidural spinal cord stimulation during stimulation at $T_9/T_{10}$ alone, $T_{13}/L_1$ alone, and combined stimulation of both areas in accordance with the present invention wherein it can be seen that combined stimulation of both areas resulted in significantly greater changes in airway pressure compared to stimulation at either area alone.
Figure 15:
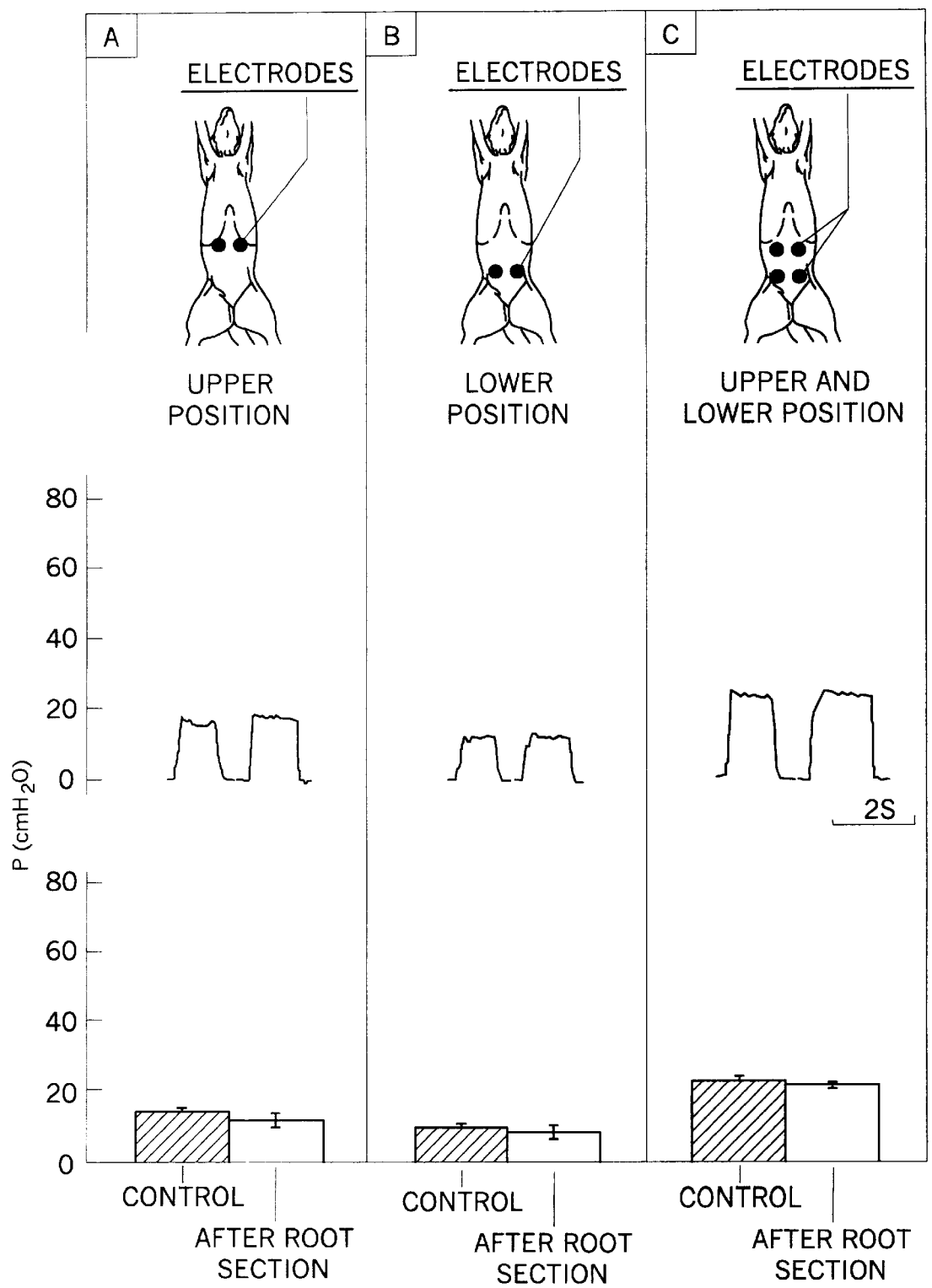
FIG. 15 illustrates the effects of surface stimulation over the anterior abdominal wall on airway pressure generation with 2 and 4 electrodes before and after spinal root section ($T_8$ through $L_2$) wherein maximal electrical stimulation resulted in only small changes in airway pressure (root section had no effect on pressure generation); and, FIG. 16 illustrates the effects of surface stimulation over the spinal roots posteriorly with 2 and 4 electrodes before and after spinal root section. Maximal surface stimulation over the spinal roots resulted in larger changes in airway pressure compared to surface stimulation over the anterior abdominal wall. Spinal root section resulted in a decrease in pressure generation indicating that spinal cord pathways contributed to the observed changes in airway pressure.
Figure 16:
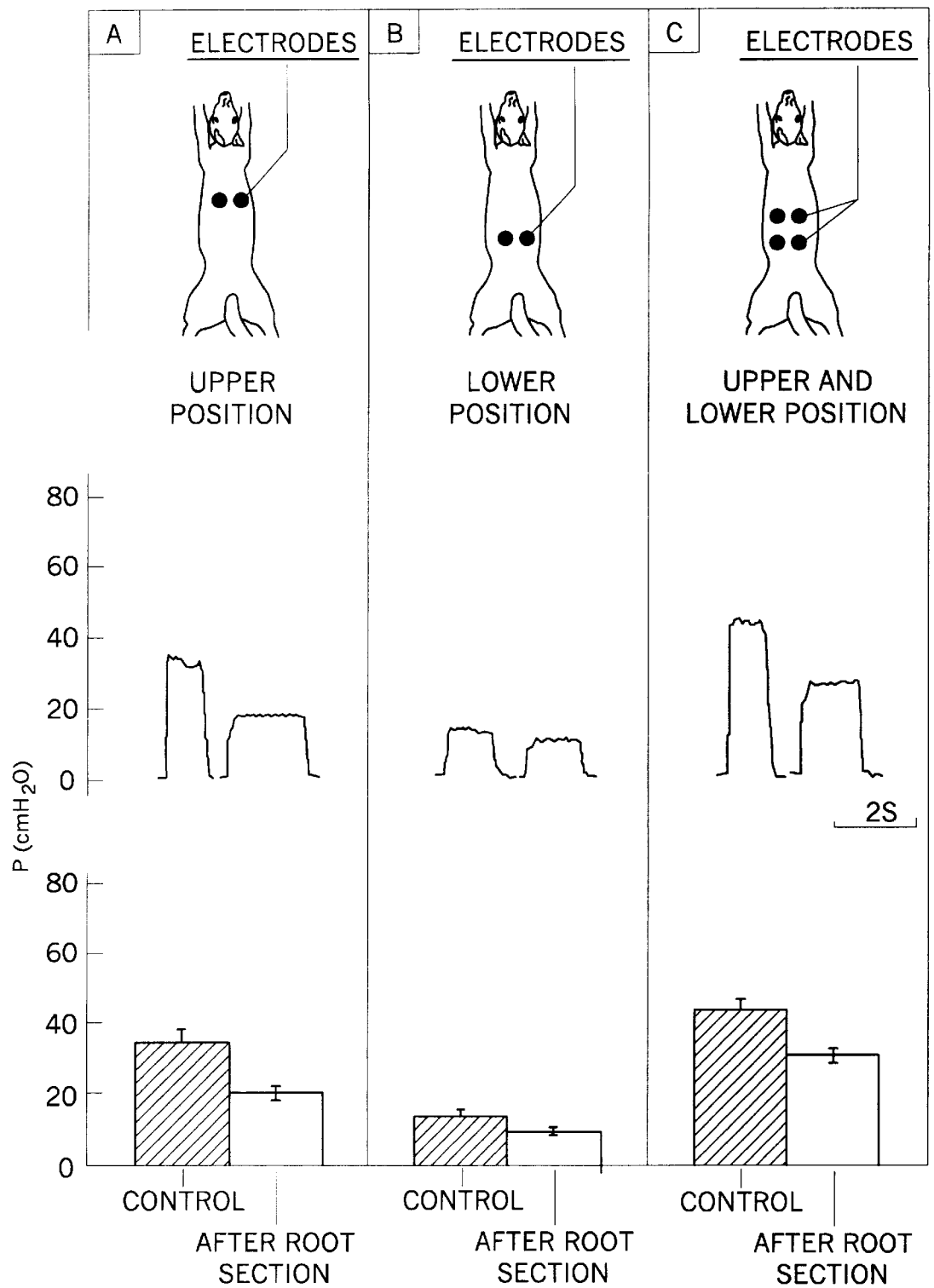

In five anesthetized supine dogs, changes in airway pressure (P) were monitored during airway occlusion and supramaximal stimulation applied during: a) spinal cord stimulation (SCS) at $T_9$/$T_{10}$, $T_{13}$/$L_1$, and combined stimulation at both sites (FIG. 14); b) electrical stimulation applied over the surface of the anterior abdominal wall (SA) with 2 electrodes positioned in the anterior axillary line bilaterally 2–3 cm below the costal margin and 2 electrodes positioned in the anterior axillary line 1 cm above the pelvic brim, and combined stimulation at both sites (FIG. 15); and, c) electrical surface stimulation of the spinal nerves (SN) with 2 electrodes positioned between the $9^{th}$ and $10^{th}$ ribs posteriorly just lateral to the midline and 2 electrodes positioned over the $T_{13}$/$L_1$ spinal roots just lateral to the midline, and combined stimulation at both sites (FIG. 16). Electrical stimulation was repeated following spinal root section ($T_8$ through $L_2$) during SA and SN. During SCS, electrical stimulation resulted in P=60 cm $H_2O\pm3$ SE, 19 cm $H_2O\pm4$ SE, and 77 cm $H_2O\pm3$ SE during stimulation at $T_9$/$T_{10}$, $T_{13}$/$L_1$, and combined stimulation at these sites, respectively. During SA, electrical stimulation resulted in P=14 cm $H_2O\pm1$ SE, 10 cm $H_2O\pm1$ SE, and 23 cm $H_2O\pm1$ SE during stimulation of the upper portion, lower portion, and combined stimulation at both sites, respectively. Spinal root section during SA had no effect on changes in P. During SN, electrical stimulation resulted in P=24 cm $H_2O\pm4$ SE, 13 cm $H_2O\pm2$ SE, 43 cm $H_2O\pm3$ SE during stimulation at the $T_9$/$T_{10}$, $T_{13}$/$L_1$, and combined stimulation at both sites, respectively, Spinal root section resulted in a significant fall in P during SN. For example, during upper and lower SN, P fell to 30 cm $H_2O\pm3$ SE (p<0.05). Therefore, SN (like SCS as demonstrated in prior studies) also involves spinal cord pathways. These results also indicate that SCS is superior to SN as a means of producing changes in P, which is, in turn, superior to SA.

By these results, it shown that: a) epidural spinal cord stimulation (SCS) is superior to surface stimulation of spinal nerves (SN) which, in turn, is superior to surface stimulation of the abdominal wall (SA), in terms of airway pressure generation, and b) as with epidural spinal cord stimulation, surface stimulation of the spinal nerves results in activation of spinal cord pathways.

An example of a suitable stimulation apparatus for applying the electrical stimulation pulses to the epidural electrodes as described above is set forth in detail in U.S. Pat. No. 5,678,535 issued to Anthony F. DiMarco, the disclosure of which is expressly incorporated by reference herein. Most preferably, a stimulator apparatus for carrying out the method of the present invention comprises a patient-implanted radio-frequency (RF) receiver and stimulation pulse generator connected to the stimulation electrodes. A battery-powered external stimulation controller includes an RF antenna for transcutaneously transmitting RF stimulation control signals and energy into the implanted RF receiver-stimulator so that the receiver-stimulator selectively passes electrical stimulation pulses to the implanted electrodes in accordance with the RF signal. Those of ordinary skill in the art will recognize that the present expiratory muscle stimulation method to produce cough may be combined with the method for electrical stimulation of the respiratory muscles to achieve artificial ventilation in a patient as described in the aforementioned U.S. Pat. No. 5,678,535.

The invention has been described with reference to preferred embodiments. Obviously, modifications and alterations will occur to others upon reading and understanding the preceding specification. It is intended that the invention be construed as including all such modifications and alterations insofar as they come within the scope of the appended claims or the equivalents thereof.

Having thus described the preferred embodiments, the invention is now claimed to be:

1. A method of electrically activating expiratory muscles of a human patient to produce cough, comprising the steps of:
   (a) positioning at least a first epidural electrode at a first location on the dorsal surface of a spinal cord of the patient; and,
   (b) selectively passing electrical stimulation pulses to said at least first epidural electrode to activate expiratory muscles of the patient to produce cough.

2. The method of electrically activating expiratory muscles of a human patient to produce cough as set forth in claim 1 comprising:
   positioning a first epidural electrode on the dorsal surface of the spinal cord of the patient in the region of the $T_9$–$T_{10}$ spinal cord level for spinal cord pathway stimulation; and,
   positioning a second epidural electrode on the dorsal surface of the spinal cord of the patient at a different spinal cord level than the first epidural electrode.

3. The method of electrically activating expiratory muscles of a human patient to produce cough as set forth in claim 2 comprising the step of positioning the second epidural electrode on the dorsal surface of the spinal cord of the patient in the region of the lower thoracic spinal root.

4. The method of electrically activating expiratory muscles of a human patient to produce cough as set forth in claim 3 wherein the second epidural electrode is positioned in the region of the $T_{12}$–$L_1$ spinal cord level.

5. The method of electrically activating expiratory muscles of a human patient to produce cough as set forth in claim 4, wherein step (b) comprises substantially simultaneously passing electrical stimulation pulses to said first and second epidural electrodes for synchronous activation of patient musculature of both the upper and lower portions of the patient abdominal wall.

6. The method of electrically activating expiratory muscles of a human patient to produce cough as set forth in claim 5 wherein step (b) comprises substantially simultaneously passing electrical stimulation pulses to said first and second epidural electrodes at a frequency in the range of approximately 20 Hz–50 Hz with a stimulus pulse amplitude in the range of approximately 10 mA–40 mA.

7. The method of electrically activating expiratory muscles of a human patient to produce cough as set forth in claim 5, further comprising the steps of:
  implanting a radio-frequency receiver and stimulation pulse generator in said patient; and,
  electrically connecting said first and second epidural electrodes to said implanted pulse generator;
  wherein step (b) further comprises using an external stimulation pulse controller to transcutaneously transmit radio-frequency stimulation pulse commands to said implanted radio-frequency receiver.

8. The method of electrically activating expiratory muscles of a human patient to produce cough as set forth in claim 2 wherein step (b) comprises substantially simultaneously passing electrical stimulation pulses to said first and second epidural electrodes at a frequency in the range of approximately 20 Hz–50 Hz with a stimulus pulse amplitude in the range of approximately 10 mA–40 mA.

9. The method of electrically activating expiratory muscles of a human patient to produce cough as set forth in claim 2 further comprising the step of positioning a third epidural electrode on the dorsal surface of the spinal cord of the patient at a location between the first and second electrodes.

10. The method of electrically activating expiratory muscles of a human patient to produce cough as set forth in claim 9, further comprising the steps of:
  implanting a radio-frequency receiver and stimulation pulse generator in said patient; and,
  electrically connecting said first, second, and third epidural electrodes to said implanted pulse generator;
  wherein said step (b) comprises using an external stimulation pulse controller to transcutaneously transmit radio-frequency stimulation pulse commands to said implanted radio-frequency receiver so that electrical stimulation pulses are at least substantially simultaneously passed from said pulse generator to at least two of said electrodes.

11. The method of electrically activating expiratory muscles of a human patient to produce cough as set forth in claim 10 wherein step (b) comprises at least substantially simultaneously passing electrical stimulation pulses from said pulse generator to said first, second, and third electrodes.

12. The method of electrically activating expiratory muscles of a human patient to produce cough as set forth in claim 1, further comprising the steps of:
  implanting a radio-frequency receiver and stimulation pulse generator in said patient; and,
  electrically connecting said at least first epidural electrode to said implanted pulse generator;
  wherein step (b) comprises using an external stimulation pulse controller to transcutaneously transmit radio-frequency stimulation pulse commands to said implanted radio-frequency receiver.

* * * * *